US012611204B2

(12) United States Patent
Islam

(10) Patent No.: US 12,611,204 B2
(45) Date of Patent: Apr. 28, 2026

(54) BONE MARROW ASPIRATION AND TREPHINE BIOPSY SINGLE NEEDLE ASSEMBLY

(71) Applicant: Abul Bashar Mohammad Anwarul Islam, Amherst, NY (US)

(72) Inventor: Abul Bashar Mohammad Anwarul Islam, Amherst, NY (US)

( * ) Notice: Subject to any disclaimer, the term of this patent is extended or adjusted under 35 U.S.C. 154(b) by 581 days.

(21) Appl. No.: 18/115,230

(22) Filed: Feb. 28, 2023

(65) Prior Publication Data

US 2024/0285265 A1      Aug. 29, 2024

(51) Int. Cl.
*A61B 10/02* (2006.01)
*A61B 17/34* (2006.01)

(52) U.S. Cl.
CPC ........ *A61B 10/025* (2013.01); *A61B 10/0283* (2013.01); *A61B 17/3417* (2013.01); *A61B 2010/0258* (2013.01); *A61B 2017/3454* (2013.01)

(58) Field of Classification Search
CPC .............. A61B 10/025; A61B 10/0283; A61B 17/3417; A61B 2010/0258; A61B 2017/3454
See application file for complete search history.

(56) References Cited

U.S. PATENT DOCUMENTS

| | | | | |
|---|---|---|---|---|
| 4,543,966 A | * | 10/1985 | Islam .................... | A61B 10/025 |
| | | | | 600/567 |
| 5,203,866 A | * | 4/1993 | Islam ..................... | A61B 17/34 |
| | | | | 606/186 |
| 5,368,046 A | * | 11/1994 | Scarfone .............. | A61B 10/025 |
| | | | | 604/117 |
| 2004/0249306 A1 | * | 12/2004 | Islam ................... | A61B 10/025 |
| | | | | 600/567 |
| 2012/0095440 A1 | * | 4/2012 | Islam ................ | A61M 39/0247 |
| | | | | 604/506 |
| 2016/0030013 A1 | * | 2/2016 | Harrison, IV ......... | A61B 10/04 |
| | | | | 600/567 |
| 2017/0119359 A1 | * | 5/2017 | Islam ................. | A61B 10/0266 |
| 2018/0117262 A1 | * | 5/2018 | Islam ................. | A61B 10/0283 |

FOREIGN PATENT DOCUMENTS

| | | | | |
|---|---|---|---|---|
| CN | 218899526 U | * | 4/2023 | |
| EP | 3659520 B1 | * | 11/2023 | .............. A61B 46/10 |
| FR | 3013958 A1 | * | 6/2015 | ........... A61B 10/025 |
| GB | 2130890 A | * | 6/1984 | ........... A61B 10/025 |

* cited by examiner

*Primary Examiner* — Jeffrey G. Hoekstra

(74) *Attorney, Agent, or Firm* — Law Office of Vincent LoTempio PLLC; Vincent G. LoTempio; Robert L. Cerasa

(57) ABSTRACT

A single needle assembly enables to obtain bone marrow aspiration and trephine biopsy specimens from the right or left posterior ilium at the same time and through the same puncture site while also maintaining the specimen quality. The operator obtains a firm grip on the single needle assembly using a T-shaped ergonomically designed handle. The distal end of the needle comprises one or more holes between the one or more external serrations and one or more sharp cutting facets. The proximal end of the trocar comprises a plastic knob wherein at the top of the knob is a connector further comprising external threads to attach a syringe or a small plastic Luer-lock cap. An insertion aid enables the operator to align the mouth of the needle and a pusher rod to propel a trephine biopsy specimen from the lumen of the needle.

4 Claims, 14 Drawing Sheets

700

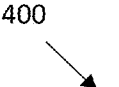
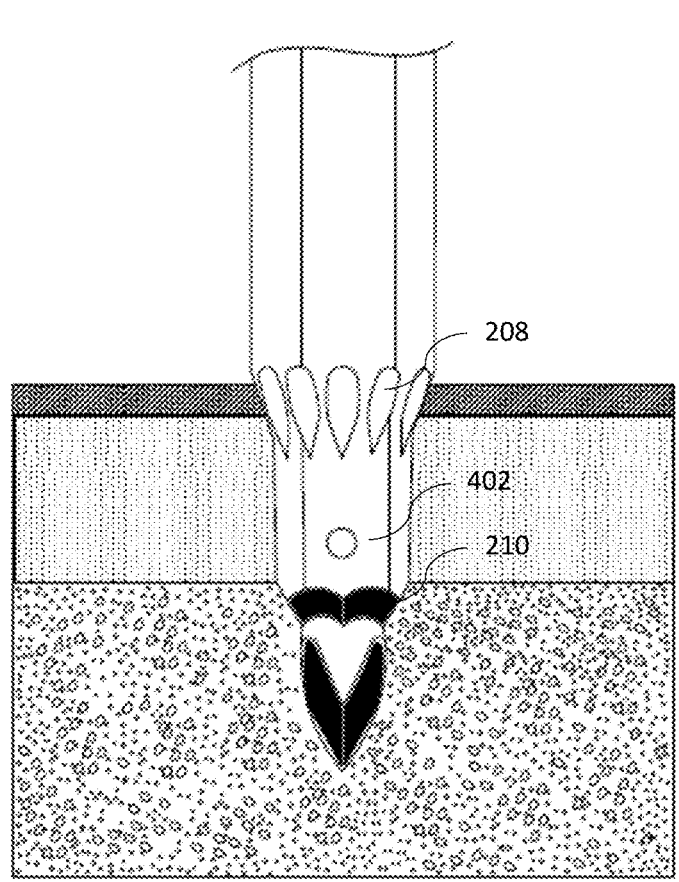
FIG. 4

502

106

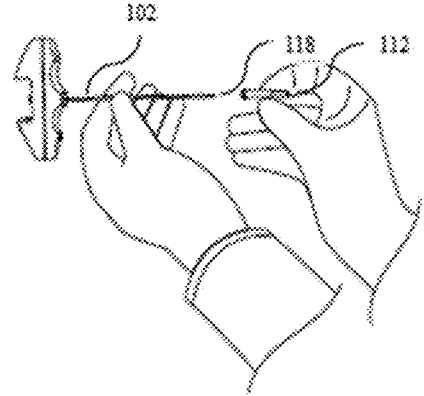
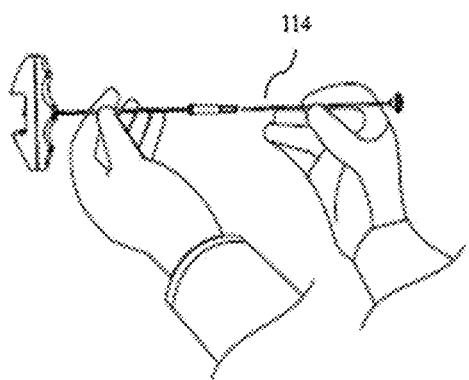
FIG. 6A                                        FIG. 6B

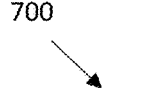
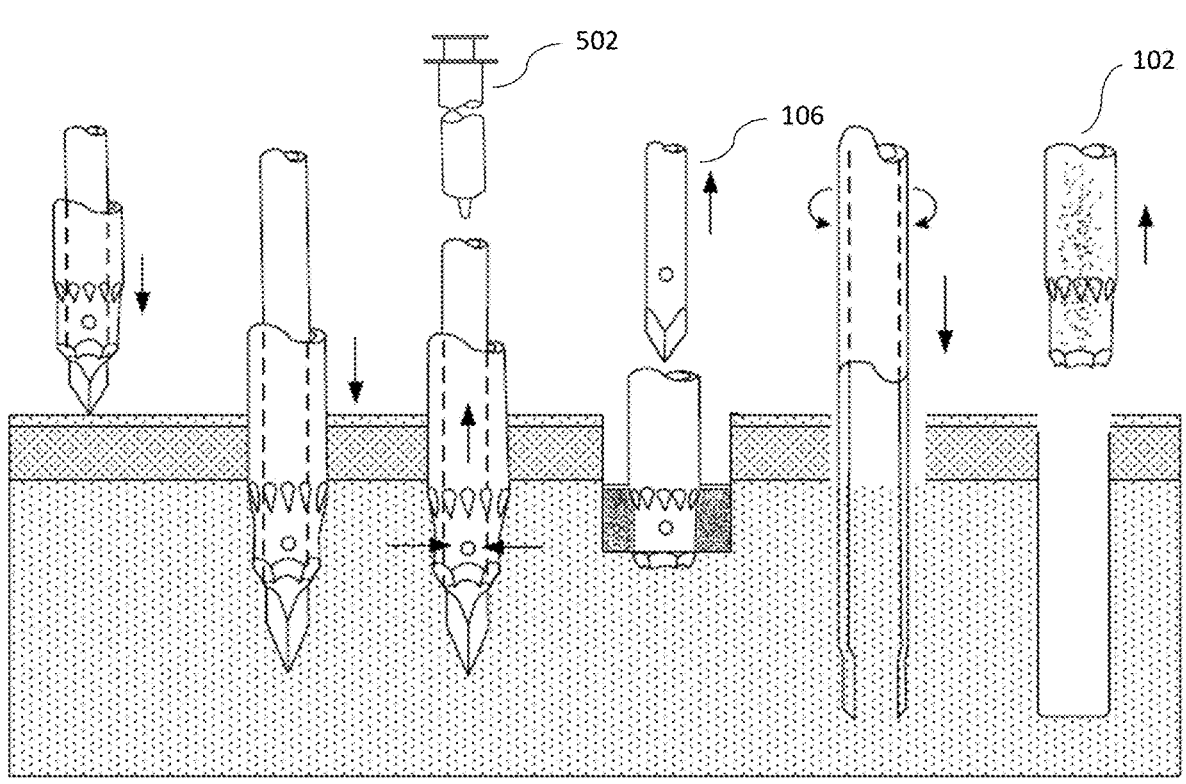
FIG. 7

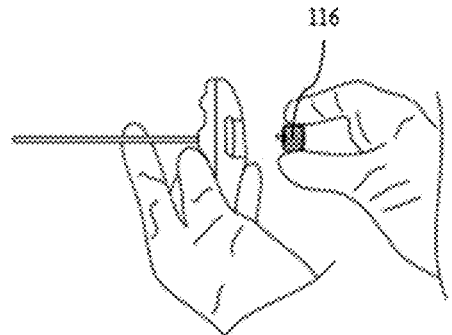
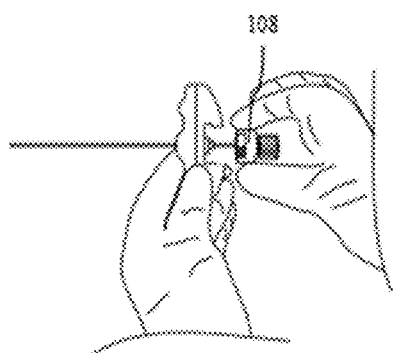
FIG. 9A
FIG. 9B

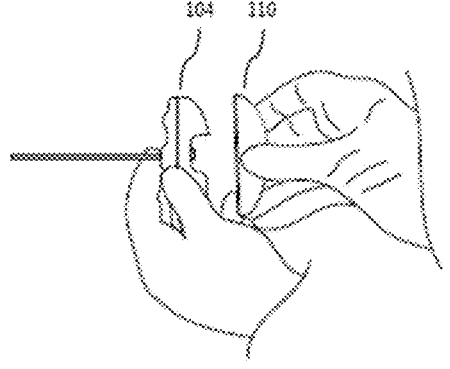
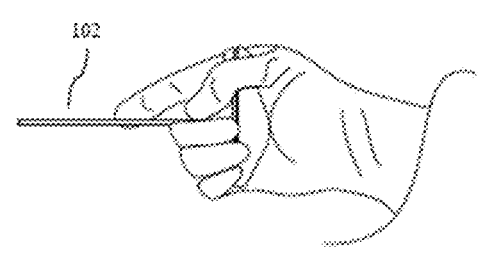
FIG. 10A                    FIG. 10B

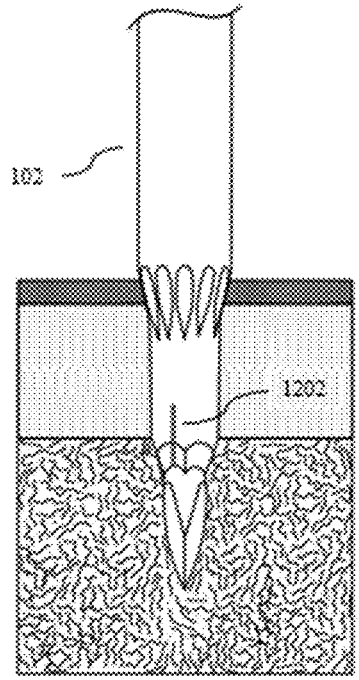
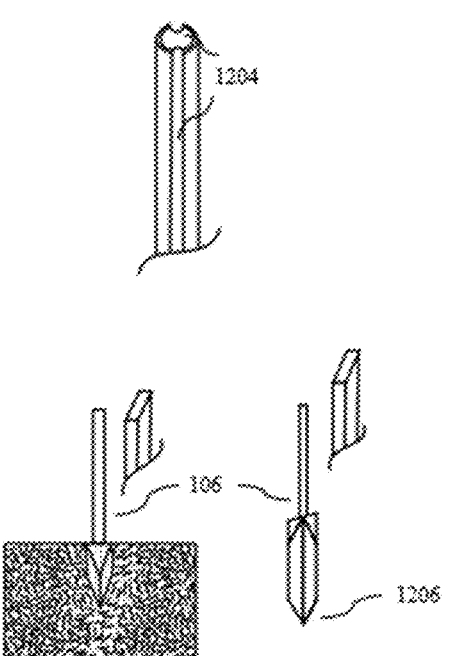
FIG. 12A                    FIG. 12B

BONE MARROW ASPIRATION AND TREPHINE BIOPSY SINGLE NEEDLE ASSEMBLY

FIELD OF THE INVENTION

The present invention relates to a single needle assembly for use in taking a bone marrow aspiration and trephine biopsy specimens from a posterior iliac crest of a patient.

BACKGROUND OF THE INVENTION

Hematological and non-hematological disorders are major health problems among the world population. These disorders are of huge concern from an individual as well as a medical point of view. Over the past few decades, there have been significant improvements in care for patients suffering from hematological and non-hematological disorders. Despite the immense and remarkable progress in this field, there are still some substantial challenges that need more research and improvements to eventually upgrade the quality of life by providing better diagnosis and treatment options. Painless diagnosis, treatments and accurate results are very crucial that further make the job easier for a medical professional as well.

Bone marrow examination plays a major role in the investigation, diagnosis, and management of patients with various hematological as well as non-hematological disorders wherein the bone marrow examination involves cyto-morphological evaluation of aspirated cells along with the histopathological evaluation of a trephine biopsy specimen. In the past, the bone marrow aspiration collection was performed using a sternal puncture needle wherein the bone marrow aspiration was obtained from either the sternum or the posterior iliac crests. The sternal puncture needle is a hollow needle that is inserted into the manubrium or the body of the sternum to obtain bone marrow aspiration. Over time, the collection of bone marrow aspiration and trephine biopsy specimens changed from the sternum to the posterior iliac crests. The collection of bone marrow aspiration and trephine biopsy specimens from the posterior iliac crests proved to provide a much lesser risk, easily accessible, and larger volume of bone marrow aspirates. Another main reason for this change is the improvement in bone marrow aspiration needles. The one or two needle technique replaced the sternal puncture technique to collect bone marrow aspiration and trephine biopsy specimens wherein the one needle technique involves using the same bone marrow biopsy needle at the same site for specimen collection. The two-needle technique on the other hand involves obtaining bone marrow aspiration using a smaller diameter aspiration needle and using a larger diameter trephine biopsy needle (a separate needle) to collect trephine biopsy specimen from the same entry point but at a different angle. The two-needle technique is observed to be a better option as compared to the one needle technique but it is time-consuming, requires two separate procedures, and is not cost-effective.

Therefore, the present invention has provided a new single-use needle to perform both bone marrow aspiration and a trephine biopsy simultaneously from the same puncture site without degrading the quality of either the bone marrow aspirate or the trephine biopsy specimen.

SUMMARY OF THE INVENTION

The present invention provides a bone marrow aspiration and trephine biopsy needle assembly. The needle assembly comprises a hollow needle for obtaining bone marrow aspiration and trephine biopsy specimen, wherein the hollow needle has a proximal end and a distal end, a handle attached to the proximal end of the hollow needle, and a distal cutting end of the hollow needle provides a frustoconical transition between the proximal end and the distal end of the hollow needle. The distal cutting end has one or more external serrations and one or more sharp cutting facets circumferentially around the distal cutting end. One or more holes are located between the one or more external serrations and one or more sharp cutting facets. A trocar is inserted into the hollow needle from the proximal end of the hollow needle so that a distal end of the trocar projects from the distal end of the needle. A solid knurled knob is attached to a proximal end of the trocar. The knob has a connector enabled to attach a Luer-lock or anon-Leuer-lock syringe and also to attach a small knurled plastic cap.

In one exemplary embodiment, wherein one or more external serrations and one or more sharp cutting facets are spaced apart circumferentially around the distal cutting end of the hollow needle.

In another exemplary embodiment, the distal cutting end is of a reduced diameter both internally and externally, when compared with the proximal end.

In yet another exemplary embodiment, the needle assembly further comprises a cap enabled to attach to a handle of the hollow needle.

BRIEF DESCRIPTION OF THE DRAWINGS

Embodiments of the present invention described herein are exemplary, and not restrictive. Embodiments will now be described, by way of examples, with reference to the accompanying drawings. In these drawings, each identical or nearly identical component that is illustrated in various figures is represented by a reference number. For purposes of clarity, not every component is labeled in every drawing. The drawings are not necessarily drawn to scale, with emphasis instead being placed on illustrating various aspects of the techniques and devices described herein.

The foregoing and other objects, aspects, and advantages are better understood from the following detailed description of a preferred embodiment of the invention with reference to the drawings, in which:

FIG. 4 shows a schematic view of a distal end of an assembled needle, in accordance with an exemplary embodiment of the present invention.

FIGS. 6A and 6B show a diagram explaining an attachment of a pusher rod to the mouth of the needle using an insertion aid, in accordance with an exemplary embodiment of the present invention.

FIG. 7 shows a schematic view of a bone marrow aspiration and trephine biopsy method, in accordance with an exemplary embodiment of the present invention.

FIGS. 9A and 9B show a diagram explaining an attachment of a small plastic Luer-lock cap to the connector at the top of the trocar knob and its (trocar and the small plastic cap) withdrawal, in accordance with an exemplary embodiment of the present invention.

FIGS. 10A and 10B show a diagram explaining a replacement of the plastic cap and the advancement of the needle into the marrow cavity to obtain the trephine biopsy specimen, in accordance with an exemplary embodiment of the present invention.

FIGS. 12A and 12B illustrate a schematic view of the distal end of the assembled needle and a trocar, in accordance with an exemplary embodiment of the present invention.

DETAILED DESCRIPTION OF THE INVENTION

In the following description, for purposes of explanation, numerous specific details are set forth in order to provide a thorough understanding of the invention. It will be apparent, however, to one skilled in the art that the invention can be practiced without these specific details. In other instances, structures, devices, activities, methods, and processes are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

The present invention discloses a device capable of performing both bone marrow aspiration and trephine biopsy at the same time using the same single needle assembly and using the same puncture (entry) site while also maintaining the specimen quality.

Figure 1:
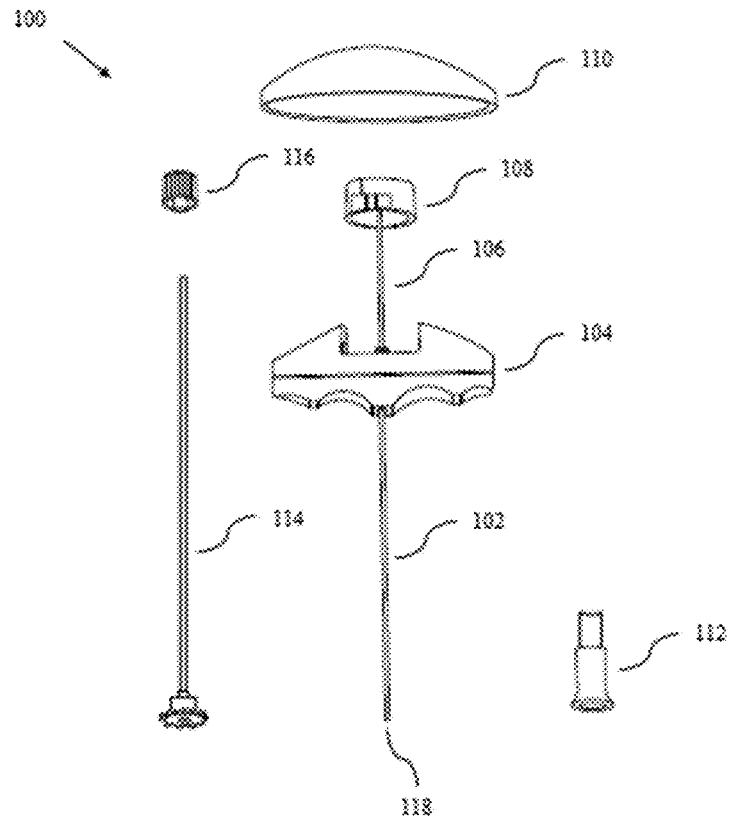
FIG. 1 shows an exploded view of a bone marrow aspiration and trephine biopsy single needle assembly, in accordance with a preferred embodiment of the present invention.

FIG. 1 shows an exploded view (100) of a bone marrow aspiration and trephine biopsy single needle assembly, in accordance with a preferred embodiment of the present invention. The bone marrow aspiration and trephine biopsy single needle assembly comprise a needle (102), a transverse plastic handle (104), a trocar (106), a plastic knob (108), a large plastic cap (110), an insertion aid (112), a pusher rod (114), a small plastic Luer-lock cap (116) and a mouth (118) of the needle (102). The needle (102) is enabled to obtain the bone marrow aspiration and trephine biopsy specimen through a skin incision of about 3 mm made by an operator with a sharp-pointed scalpel blade. The bone marrow aspiration and trephine biopsy specimens are obtained from a posterior iliac crest. The needle (102) has a length of about 70-125 mm, a uniform external diameter of 3.30 mm, and a constant internal diameter of 2.9 mm. A distal cutting end of the needle (102) is narrowed wherein the diameter of the distal cutting end of the needle (102) is about 3.0 mm. The transverse plastic handle (104) is T-shaped and is ergonomically designed enabling it to provide a comfortable firm grip to an operator and further improving the maneuverability of the bone marrow aspiration and trephine biopsy single needle assembly during the biopsy procedure. The handle (104) is further enabled to provide a comfortable experience to an operator. The trocar (106) is a centrally hollowed-out shaft of about 2.1 mm in diameter. The distal end of the trocar (106) is sharply-pointed having a diameter of about 3.0 mm wherein the distal end of the trocar (106) projects beyond the cutting edge of the needle (102). The trocar (106) is further enabled to provide means of easy penetration of the skin, soft tissue, and dense cortical bone. Further, a proximal end of the trocar (106) is fitted with the knurled plastic knob (108) wherein the top of the knob (108) is fitted further with a connector (not shown) that comprises external threads (not shown) to facilitate attachment of a Luer-lock syringe.

The external thread (not shown) is enabled to receive the nozzle of a Leuer-lock syringe for bone marrow aspiration. The large plastic cap (110) is enabled to provide handling comfort to the operator during the biopsy procedure and further, fits and covers the top of the transverse plastic handle (104). The insertion aid (112) is enabled to provide easy removal of the biopsy specimen through the proximal end of the needle (102). The height of the insertion aid (112) is about 30 mm. The central area of the front portion of the insertion aid (112) is hollow and is enabled to receive and tightly fit the distal cutting end of the needle (102). The central area of the rear portion is hollow as well which is enabled to receive and provide proper alignment of the pusher rod (114) with the mouth (118) of the needle (102). The distal end of the pusher rod (114) is chamfer-shaped which enables it to enter the mouth (118) of the needle with case (102). The pusher rod (114) is enabled to easily enter the mouth (118) of the needle (102) even in the presence of extra bony soft tissue that may cover the mouth (118) of the needle. The pusher rod (114) is enabled to provide means of easy dislodgement and extrusion of the biopsy specimen through the proximal end of the needle (102). The small plastic Luer-lock cap (116) is fitted at a proximal end of the trocar (106) enabling the Luer-lock cap (116) to close the distal opening at the trocar (106) to avoid spilling of marrow and blood following bone marrow aspiration.

Figure 2:
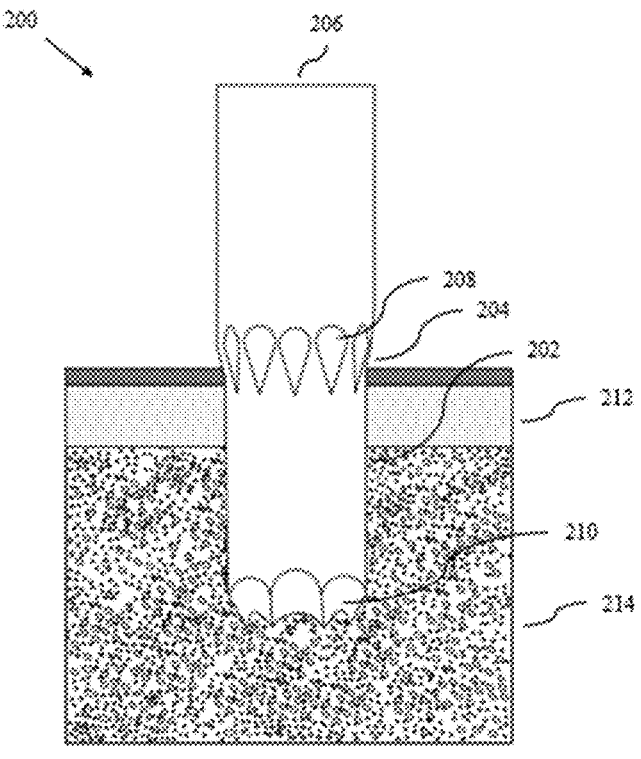
FIG. 2 shows a schematic view of the distal cutting end of a needle, in accordance with an exemplary view of the present invention.

FIG. 2 shows a schematic view (200) of the distal cutting end (202) of the needle (102), in accordance with an exemplary view of the present invention. The distal cutting end (202) of the needle (102) has a first internal diameter of about 2.1 mm and provides a frustoconical transition (204) between the proximal end and the distal end of the needle (102). The first internal diameter of the distal cutting end (202) of the needle (102) is less than a second internal diameter of the proximal end (206) of the needle (102). The distal end of the needle (102) comprises one or more external serrations (208) and one or more sharp cutting facets (210). One or more external serrations (208) are enabled to facilitate the needle (102) to cut through the dense cortical bone (212) and further allow an easy and smooth entry of the needle (102) into the spongy bone (214). One or more external serrations (208) are provided at the junction of the narrower distal end of the needle (102) and its adjoining wider proximal end of the needle (102). One or more external serrations (208) are enabled to provide the means of cutting through a plurality of clockwise and counter-clockwise rotations of the needle (102) through the dense cortical bone (212). One or more sharp cutting facets (210) are enabled to cut the bony trabecular cleanly.

Figure 3:
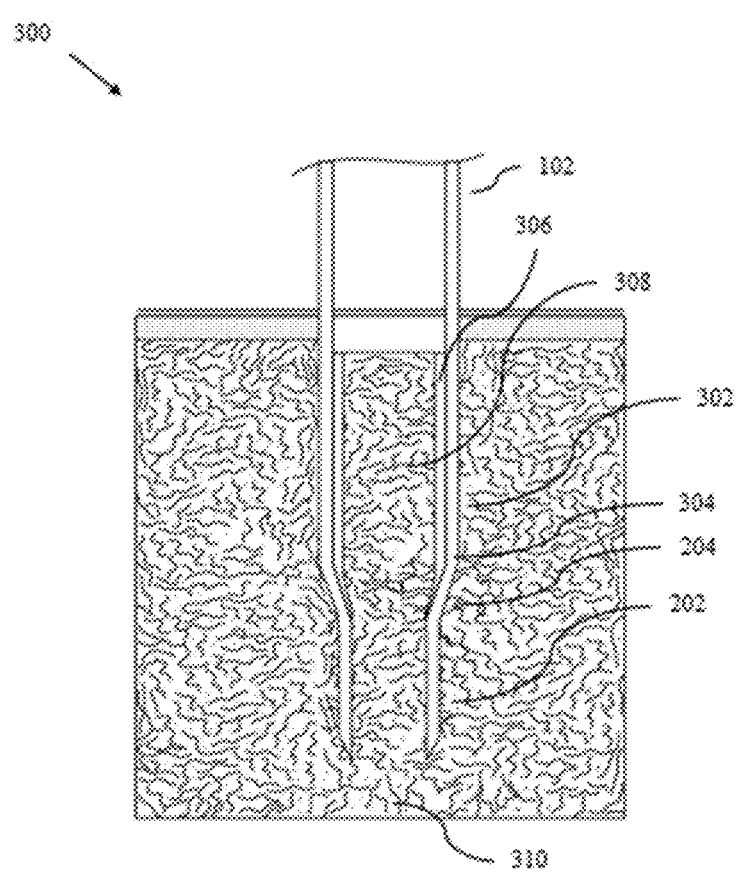
FIG. 3 shows a schematic view of the distal end of the needle, in accordance with an exemplary view of the present invention.

FIG. 3 shows a schematic view (300) of the distal end of the needle (102), in accordance with an exemplary view of the present invention. The distal end of the needle (102) comprises an outer wall (302) of the needle (102), an inner wall (304) of the needle (102), a free space (306) between the inner wall (304) of the needle (102) and a marrow core (308), a distal cutting end (202) of the needle (102) and the frustoconical transition (204). The distal cutting end (202) of the needle (102) is enabled to cut all the trabecular connections of the core at its base (310). Further, the frustoconical transition (204) is enabled to hold the trephine biopsy specimen during its extraction allowing it to not slip out of the needle (102).

FIG. 4 shows a schematic view of a distal end of an assembled needle (400), in accordance with an exemplary embodiment of the present invention. The assembled needle (400) at its distal end comprises one or more holes (402) where one or more holes (402) are located between one or more external serrations (208) and one or more sharp cutting facets (210). One or more holes (402) are enabled to provide suction and flow of marrow from the surrounding lateral side, leaving the distant marrow from where a core biopsy is obtained undisturbed.

Figure 5:
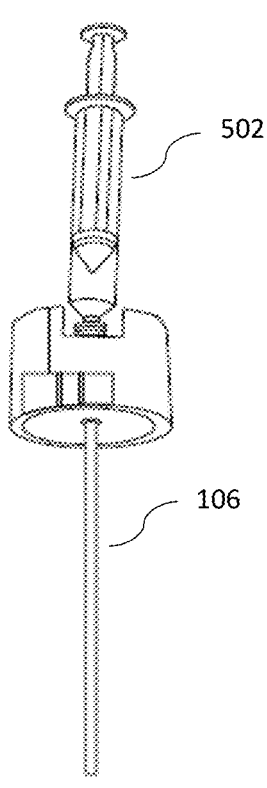
FIG. 5 shows a diagram explaining an attachment of a syringe to a connector at the top of a knob, in accordance with an exemplary embodiment of the present invention.

With reference to FIGS. 1 and 5, a proximal end of the trocar (106) that houses a knob wherein the top of the knob comprises a connector (not shown) that further comprises the external thread (not shown). The external thread (not shown) is enabled to receive and firmly attach the nozzle of a Leuer-lock syringe (502) for bone marrow aspiration. Further, the connector (not shown) at the top of the knob is enabled to allow attachment of the Luer-lock cap to prevent the spilling of marrow and blood following the bone marrow aspiration.

In one exemplary embodiment, the syringe for bone marrow aspiration can be a Luer-lock or a non-Luer-lock syringe wherein the Luer-lock or the non-Luer-lock syringe is fitted at the external thread (not shown) of the connector at the top of the knob to perform bone marrow aspiration.

With reference to FIGS. 6A and 6B, the first end of the insertion aid (112) is attached to the distal cutting end of the needle (102) and the pusher rod (114) is enabled to enter through the second end of the insertion aid (112) to remove the biopsy specimen by pushing it forward. The insertion aid (112) is enabled to provide proper alignment of the distal cutting end of the needle (102) and the pusher rod (114) and further provides easy dislodgement and removal of the biopsy specimen through the mouth (118) of the needle (102).

FIG. 7 shows a schematic view (700) of a bone marrow aspiration and trephine biopsy method, in accordance with an exemplary embodiment of the present invention. The bone marrow aspiration and trephine biopsy method include obtaining one or more bone marrow aspiration and trephine biopsy specimens from a right or left posterior iliac crest. The bone marrow aspiration and trephine biopsy specimens are obtained at the same time wherein a single bone marrow aspiration and trephine biopsy single needle assembly is enabled to perform the entire procedure. The puncture site for obtaining one or more bone marrow aspiration and trephine biopsy specimens is kept the same throughout the entire procedure. The same puncture site provides a high-quality bone marrow aspirate specimen as well as a high-quality trephine biopsy specimen that too without altering the marrow architecture of the trephine biopsy specimen. The bone marrow aspiration and trephine biopsy method further include placing the patient in a right or left lateral decubitus position with the top knee bent forward and drawn up and the back comfortably flexed or in the prone position with a pillow beneath the hips. Manual palpation or ultrasound guidance is used to identify the site of the posterior iliac crest wherein an indelible ink is enabled to mark the site of the posterior iliac crest. The area over the posterior iliac crest is prepared with betadine and alcohol wherein the area over the posterior iliac crest is then draped. A local anesthetic is infiltrated in the skin, the subcutaneous tissue, and the periosteum. A sharp-pointed scalpel blade is enabled to make a small 3 mm skin incision. The bone marrow aspiration and trephine biopsy single needle assembly are enabled to advance slowly through the incision towards the posterior iliac crest. The bone marrow aspiration and trephine biopsy single needle assembly are enabled to penetrate the posterior iliac crest by gentle rotary motions of the bone marrow aspiration and trephine biopsy single needle assembly.

Once the trocar (106) and the distal end of the needle (102) penetrate the cortex and reach a marrow cavity, the large plastic cap is removed by the operator and the syringe (502) is enabled to perform the bone marrow aspiration. Following bone marrow aspiration, the small plastic Luer-lock cap is attached to the trocar knob that enables to prevent the spilling of blood and marrow wherein the Luer-lock cap is fitted to the external threads (not shown) of the connector (not shown) at the top of the knob. The trocar (106) with the attached small plastic cap (116) is then removed by pulling it rearwards. The large plastic cap is replaced and the needle (102) is further advanced into the marrow cavity with slow, steady, and controlled clockwise-counterclockwise rotary motions. The needle is enabled to reach a depth of about 15-20 mm wherein the needle (102) is then rotated multiple times to sever all the trabecular connections at the base of a marrow core and break loose the trephine biopsy specimen from a surrounding spongy bone. The needle (102) is then pulled out (in a straight manner) by gentle alternating rotary motions. No rocking, skulling, gyratory movements, or change in the direction of the needle is necessary. The large plastic cap from the proximal end of the needle (102) is removed and the insertion aid is enabled to attach the distal cutting end of the needle and the pusher rod is introduced from the opposite end of the insertion aid. The pusher rod is enabled to remove the trephine biopsy specimen from within the lumen of the needle (102). The bone marrow aspiration and trephine biopsy method further include pressing the edges of a wound together using an adhesive tape. A gauze dressing is applied and the patient is instructed to lie flat on his/her back for about 10-15 minutes or maybe even longer depending on whether the patient has a low platelet count or other bleeding disorder or if the patient has been on aspirin or other anticoagulants.

Figure 8A:
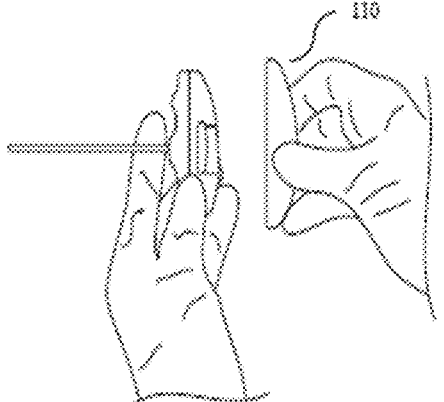
FIGS. 8A and 8B show a diagram explaining a removal of the plastic cap and attachment of the syringe, in accordance with an exemplary embodiment of the present invention.
Figure 8B:
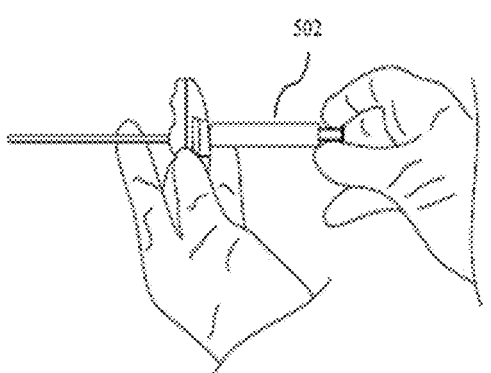

FIGS. 8A and 8B illustrate a removal of the large plastic cap (110) and attachment of the syringe (502), in accordance with an exemplary embodiment of the present invention. The plastic cap (110) is removed by the operator by pulling it off and the syringe (502) is attached to the connector (not shown) that enables the operator to perform a bone marrow aspiration.

FIGS. 9A and 9B illustrate an attachment of the small plastic Luer-lock cap (116) to the connector (not shown) at the top of the trocar knob (108) following bone marrow aspiration and the withdrawal of the trocar (106), in accordance with an exemplary embodiment of the present invention. The bone marrow aspiration and trephine biopsy single needle assembly are then advanced towards the posterior iliac crest to obtain the trephine biopsy specimen.

FIGS. 10A and 10B illustrate a replacement of the large plastic cap (110) and the advancement of the needle (102) into the marrow cavity to obtain the trephine biopsy specimen, in accordance with an exemplary embodiment of the present invention. The plastic cap (110) is enabled to provide handling comfort of the bone marrow aspiration and trephine biopsy single needle assembly to the operator wherein the large plastic cap (110) covers the top of the solid plastic transverse handle (104).

Figure 11A:
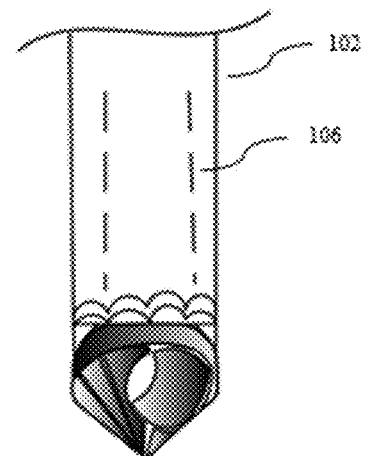
FIGS. 11A and 11B illustrate a perspective view of the needle, in accordance with an exemplary embodiment of the present invention.
Figure 11B:
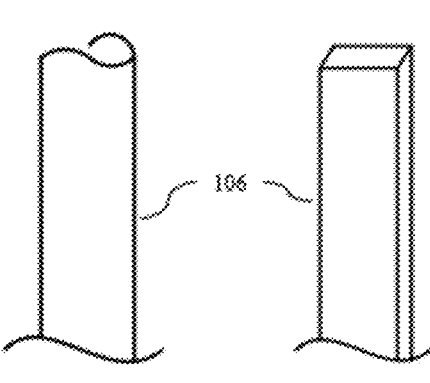

FIGS. 11A and 11B illustrate a perspective view of the needle (102), in accordance with an exemplary embodiment of the present invention. The body of the trocar (106) may be round or even flat shaped as shown in FIG. 11B.

FIGS. 12A and 12B illustrate a schematic view of the distal end of the needle (102) and a trocar (106), in accordance with an exemplary embodiment of the present invention. The distal cutting end of the needle (102) may comprise one or more slits (1202) instead of one or more holes. The body of the trocar (106) can be a solid flat metal bar enabled to provide free space on either side of the solid flat metal bar and the inner wall of the needle (102) for bone marrow aspiration. With reference to FIG. 12B, each side of the body of the trocar (106) comprises one or more continuous rooves (1204). Further, the tip (1206) of the trocar (106) can be pointed or even diamond-shaped.

Figure 13:
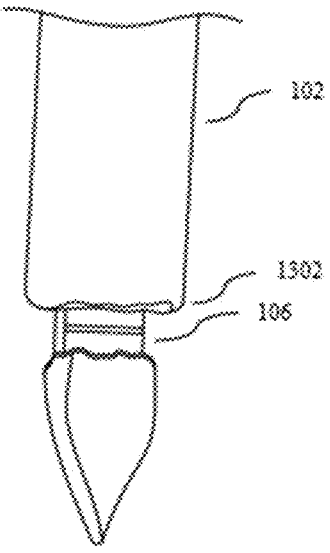
FIG. 13 illustrates a schematic view of the distal end of the assembled needle, in accordance with an exemplary embodiment of the present invention.

FIG. 13 illustrates a schematic view of the distal end of the assembled needle, in accordance with an exemplary embodiment of the present invention. The solid flat metal bar body of the trocar (106) protrudes from the cutting end (1302) of the needle (102). Further, the distal end of the trocar (106) easily penetrates the skin, soft tissue, and dense cortical bone.

Figure 14:
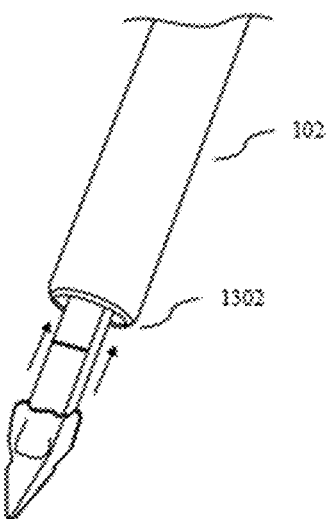
FIG. 14 illustrates a schematic view of a distal end of an assembled needle, in accordance with an exemplary embodiment of the present invention.

FIG. 14 illustrates a schematic view of a distal end of an assembled needle, in accordance with an exemplary embodiment of the present invention. The bone marrow enters the distal end of the needle (102) through the cutting end (1302) of the needle (102).

Although the present invention has been described with reference to specific exemplary embodiments, it will be evident that the various modifications and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A bone marrow aspiration and trephine biopsy needle assembly comprising: a hollow needle for obtaining a bone marrow aspiration and a solid trephine biopsy specimen, wherein the hollow needle having a proximal end and a distal end, a handle attached to the proximal end of the hollow needle; a distal cutting end of the hollow needle provides a frustoconical transition between the proximal end and the distal end of the hollow needle; that forms an internal shoulder configured to retain the solid trephine biopsy specimen, and wherein the hollow needle further comprises one or more side holes located proximally to the distal cutting end; wherein the distal cutting end has one or more external serrations and one or more sharp cutting facets circumferentially around the distal cutting end; a cannulated trocar having an internal lumen extending therethrough, the cannulated trocar being removably inserted into the hollow needle from the proximal end of the hollow needle, so that a distal end of the trocar projects from the distal end of the needle, and wherein the one or more side holes are configured to provide a fluid pathway for lateral aspiration from a bone marrow space into the internal lumen of the cannulated trocar; and a knob attached to a proximal end of the trocar; wherein the knob has a connector enabled to attach a luer lock cap; and wherein the bone marrow aspiration and solid trephine biopsy specimens are configured to be obtained with a single insertion of said biopsy needle assembly.

2. The bone marrow aspiration and trephine biopsy needle assembly of claim 1, further comprising: a cap enabled to attach to a handle of the hollow needle.

3. The bone marrow aspiration and trephine biopsy needle assembly of claim 1, wherein the one or more external serrations and one or more sharp cutting facets are spaced apart circumferentially around the distal cutting end of the hollow needle.

4. The bone marrow aspiration and trephine biopsy needle assembly of claim 1, wherein the distal cutting end being of a reduced diameter both internally and externally, when compared with the proximal end.

* * * * *